(12) United States Patent
Blumenfeld et al.

(10) Patent No.: US 8,440,833 B2
(45) Date of Patent: *May 14, 2013

(54) HUMAN PAPILLOMA VIRUS INHIBITORS AND PHARMACEUTICAL COMPOSITIONS CONTAINING SAME

(75) Inventors: Marta Blumenfeld, Paris (FR); Delphine Compere, Sceaux (FR); Jean-Michel Gauthier, Conflans-Sainte-Honorine (FR)

(73) Assignee: Anaconda Pharma, Paris (FR)

( * ) Notice: Subject to any disclaimer, the term of this patent is extended or adjusted under 35 U.S.C. 154(b) by 232 days.

This patent is subject to a terminal disclaimer.

(21) Appl. No.: 12/743,742

(22) PCT Filed: Nov. 20, 2008

(86) PCT No.: PCT/EP2008/065915
§ 371 (c)(1), (2), (4) Date: Jul. 8, 2010

(87) PCT Pub. No.: WO2009/065893
PCT Pub. Date: May 28, 2009

(65) Prior Publication Data
US 2010/0286162 A1    Nov. 11, 2010

(30) Foreign Application Priority Data
Nov. 20, 2007   (FR) ..................... 07 59175

(51) Int. Cl.
*C07D 211/08*     (2006.01)
*A61K 31/4453*    (2006.01)

(52) U.S. Cl.
USPC ....... 546/231; 544/360; 514/253.01; 514/331

(58) Field of Classification Search .............. 546/231; 544/360; 514/331, 253.01; 564/149
See application file for complete search history.

(56) References Cited

U.S. PATENT DOCUMENTS

| | | | | |
|---|---|---|---|---|
| 4,939,261 A * | 7/1990 | Ksander | | 514/357 |
| 6,525,094 B1 * | 2/2003 | Zhang et al. | | 514/539 |
| 8,207,373 B2 * | 6/2012 | Blumenfeld | | 562/439 |
| 2009/0208586 A1 | 8/2009 | Sajiki et al. | | |

FOREIGN PATENT DOCUMENTS

| | | |
|---|---|---|
| DE | 3723232 A1 | 1/1989 |
| FR | 2 901 273 A1 | 11/2007 |
| WO | WO 01/35900 A2 | 5/2001 |
| WO | WO 2004/108673 A2 | 12/2004 |
| WO | WO 2007/135106 A1 | 11/2007 |

OTHER PUBLICATIONS

Rautio "Prodrugs: design and clinical applications." Nature Reviews Drug Discovery Mar. 2008, vol. 7, 255.*
International Search Report issued in application No. PCT/EP2008/065915 on Jan. 14, 2009.
Wermuth, "Molecular variations based on isoteric replacements," *Practice of Medicinal Chemistry*, Chapter 13, pp. 203-237, 1996.
Berge et al., "Pharmaceutical Salts," *Journal of Pharmaceutical Sciences*, vol. 66, No. 1, pp. 1-19, Jan. 1977.
Bellamy et al., "Selective Reduction of Aromatic Nitro Compounds with Sannous Chloride in Non Acidic and Non Aqueous Medium," *Tetrahedron Letters*, vol. 25, No. 8, pp. 839-842, 1984.
Grell et al., "Repaglinide and Related Hypoglycemic Benzoic Acid Derivatives," *J. Med. Chem.*, vol. 41, pp. 5219-5246, 1998.
Chiang et al., "Viral E1 and E2 proteins support replication of homologous and heterologous papillomaviral origins," *Proc. Natl. Acad. Sci. USA*, vol. 89, pp. 5799-5803, Jul. 1992.
White et al., "Inhibition of Human Papillomavirus DNA Replication by Small Molecule Antagonists of the E1-E2 Protein Interaction," *The Journal of Biological Chemistry*, vol. 278, No. 29, pp. 26765-26772, 2003.

* cited by examiner

*Primary Examiner* — David K O Dell
(74) *Attorney, Agent, or Firm* — Foley & Lardner LLP

(57) ABSTRACT

HPV inhibitors of formula (I) in which $G_1$ is —NHCO($CH_2$)n-, where n is an integer between 1 and 4, R3 is —CW($CH_2$)$_m$—NR4R5 or —CW($CH_2$)$_m$$CH_3$ or —CN, where W is O, S or NH and m is an integer between 0 and 5, or R3 is one of the following groups: and A is an optionally substituted aryl group and B is an aryl group, preferably a phenyl which is substituted.

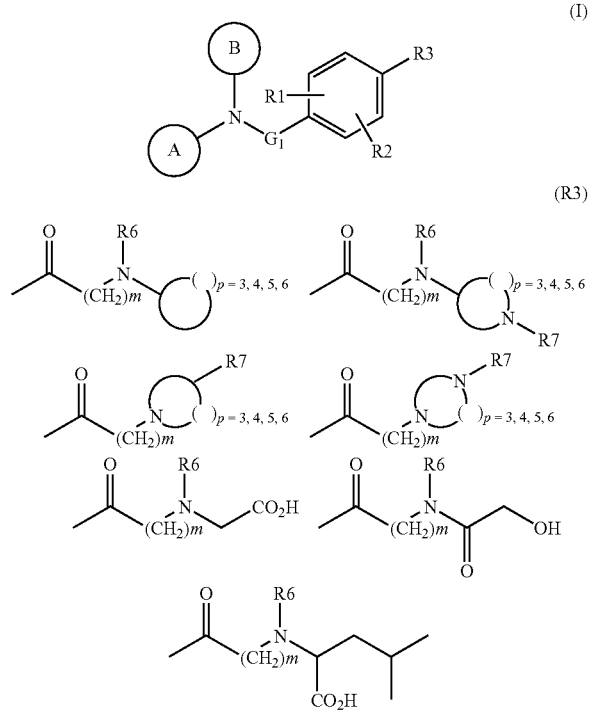

17 Claims, No Drawings

HUMAN PAPILLOMA VIRUS INHIBITORS AND PHARMACEUTICAL COMPOSITIONS CONTAINING SAME

The present invention relates to novel antiviral compounds directed against the papilloma virus, to pharmaceutical compositions containing them, to their preparation method, as well as to their use for treating or preventing infection by the papilloma virus.

The papilloma viruses are non-encapsulated viruses, the genome of which is formed by a double strand DNA of about 8 kb. They are very widespread in nature and cause epithelial lesions in humans as well as in many animals including rabbits, horses, dogs and bovine species. More than a hundred human papilloma viruses (HPV) have been described. They are classified depending on their infection site. About 30 HPVs have been isolated from anogenital mucosas (servix uteri, vagina, vulva, penis, anus, rectum). The other HPVs are associated with skin lesions. The HPVs with skin tropism include, i.a. HPV1, HPV2, HPV3, HPV4, HPV5, HPV7, HPV8, HPV9, HPV10, HPV12, HPV14, HPV15, HPV17, HPV19, HPV20, HPV21, HPV22, HPV23, HPV24, HPV25, HPV26, HPV27, HPV28, HPV29, HPV38, HPV41, HPV47, HPV49. They are associated with lesions such as verrucas (of the vulgar, plantar, myrmecia, superficial, flat type . . . ) and diseases such as verruciform epidermo-dysplasia.

HPVs of the mucogenital type are involved in laryngeal and anogenital diseases including certain cancers. They are often classified as high risk HPV and low risk HPV, by referring to the type of lesions with which they are associated. Low risk HPVs include, i.a. HPV6, HPV11, HPV13, HPV32, HPV34, HPV40, HPV42, HPV43, HPV44, HPV53, HPV54, HPV55, HPV57, HPV58, HPV74, HPV91. Low risk HPVs are associated with benign lesions such as condylomas (genital verrucas such as acuminated condylomas and planar condylomas), laryngeal, connective or buccal papillomas or other epithelial lesions such as low grade intra-epithelial neoplasias or respiratory recurrent papillomatoses, and more rarely bowenoid papuloses or high grade intra-epithelial neoplasias or carcinomas. High risk HPVs include i.a. HPV16, HPV18, HPV31, HPV33, HPV35, HPV39, HPV45, HPV51, HPV52, HPV56, HPV59, HPV61, HPV62, HPV66, HPV67, HPV68, HPV72. They are involved in low grade intra-epithelial lesions which may evolve towards lesions of higher grade ranging up to cancers, in particular the cancer of the cervix uteri and other ano-genital cancers.

Genital infections by HPVs are the most frequent sexually transmitted infections worldwide, including in developed countries, with more than 20 million persons infected in the United States. Prevalence of HPV infections vary from 3-42% depending on the countries and affects 10-20% of the sexually active population in industrialized countries. In a portion of this population, the infection persists and may lead to cancers in the case of high risk HPVs.

Prevalence of genital verrucas (condylomas) in the sexually active population of industrialized countries is estimated to be 1-2%, i.e. about 3,500,000 new cases per year in these countries and 28,000,000 worldwide. Genital verrucas may be found on portions of the body comprising or peripheral to the anus, the vulva, the vaginal, the cervix uteri and the penis.

Treatments of genital verrucas are based on several strategies, from physical destruction (cryotherapy, $CO_2$ laser, electro-surgery, surgical excision), application of cytotoxic agents (TCA, podophyllin, podofilox) up to the application of immuno-modulating agents (interferon, imiquimod, polyphenon E). However, none of these methods completely remove all the viral particles and significant recurrence rates, accompanied by serious secondary effects, are observed with present therapeutic strategies. This reinforces a need for novel strategies for controlling or eliminating the infections by the papilloma viruses.

Unlike what exists in the treatment of other viral diseases, such as those caused by the HIV, the herpes virus or the influenza viruses, today, there is no antiviral treatment specifically targeting the viral pathogens which are the papilloma viruses.

The papilloma viruses infect pluristratified epithelia and their viral cycle is closely related to organogenesis of these organs and to the differentiation of keratinocytes. After infection, the viral genome is present and replicated in small numbers in the basal cells of the epithelium. As the cells are gradually differentiated, the expression of the viral genes and the number of copies of the viral genome increase, up to the expression of the genes of the viral capsid and the formation of infectious virions in totally differentiated keratinocytes.

The genome of the HPVs potentially codes for about ten proteins. The earliest expressed proteins, E1 and E2, are involved in the replication of the viral genome and the regulation of the expression of the viral genes. The other early proteins of these viruses (E4, E5, E6, E7) have functions in connection with cell proliferation or roles which are not completely elucidated. The existence of the proteins E3 and E8 is still uncertain. Belated proteins L1 and L2 are those which form the viral capsid.

The only 2 viral proteins necessary and sufficient for replication of the HPVs are E1 and E2. They are capable of forming a complex E1/E2 and of being fixed on the replication origin (Ori) of the HPVs, a sequence contained in the viral genome and bearing close sites recognized by E1 and by E2. E2 is capable of being bound with very large affinity on the E2 sites whereas E1, alone, does not have a very large affinity for E1 sites. The interaction between E1 and E2 increases the binding of E1 on Ori by co-operative binding to DNA. Once bound on the DNA, E1 no longer interacts with E2, but forms a hexamer. The helicase and ATPase activies of E1 allow the unfolding of the viral DNA which is then replicated by the cell replication machinery. The interaction between the viral proteins E1 and E2 is absolutely necessary for the replication of the HPVs in cells. Disruption of the interaction between E1 and E2 results in absence of viral replication.

The inventors have sought to develop small molecules which inhibit replication of the HPVs, preferably low risk HPVs, by notably interfering with the formation of the complex between the proteins E1 and E2.

A solution was found for elaborating novel derivatives.

An object of the present invention is these novel derivatives, their synthesis as well as their use in pharmaceutical compositions capable of being used in preventing and treating pathologies related to an inhibition of the replication of HPVs, such as for example, HPV1, HPV2, HPV3, HPV4, HPV5, HPV7, HPV8, HPV9, HPV10, HPV12, HPV14, HPV15, HPV17, HPV19, HPV20, HPV21, HPV22, HPV23, HPV24, HPV25, HPV26, HPV27, HPV28, HPV29, HPV38, HPV41, HPV47, HPV49, HPV6, HPV11, HPV13, HPV32, HPV34, HPV40, HPV42, HPV43, HPV44, HPV53, HPV54, HPV55, HPV57, HPV58, HPV74, HPV91, HPV16, HPV18, HPV31, HPV33, HPV35, HPV39, HPV45, HPV51, HPV52, HPV56, HPV59, HPV61, HPV62, HPV66, HPV67, HPV68, HPV72 preferably low risk HPVs such as HPV6, HPV11, HPV13, HPV32, HPV34, HPV40. HPV42, HPV43, HPV44, HPV53, HPV54, HPV55, HPV57, HPV58, HPV74, HPV91.

The novel derivatives object of the present invention are active against the papilloma virus. They are also capable of inhibiting the E1/E2 interaction.

Within the scope of the present invention, the following definitions are given:

"Alkyl" or "Alk" means a monovalent or divalent linear or branched saturated hydrocarbon chain, comprising from 1 to 6 carbon atoms such as the methyl, ethyl, propyl, isopropyl, tert-butyl, methylene, ethylene, propylene groups, . . . .

"Acyl" means a —$COR_a$ group where $R_a$ is an alkyl group as defined earlier or a phenyl group, for example acetyl, ethylcarbonyl, benzoyl, . . . .

"Acylamino" means a —NHC(O)R group wherein R is an alkyl group as defined earlier.

"Acylaminoalkyl" means an -AlkNHC(O)$R_b$ group, wherein Alk and $R_b$ are alkyl groups as defined earlier.

"Alkoxy" means an —OAlk group wherein Alk is an alkyl group as defined earlier. Alkoxy for example comprises methoxy, ethoxy, n-propyloxy, tert-butyloxy, . . . .

"Aryl" means an aromatic monocyclic or bicyclic system comprising from 4 to 10 carbon atoms, it being understood that in the case of a bicyclic system, one of the cycles is aromatic and the other cycle is aromatic or unsaturated. Aryl for example comprises the phenyl, naphthyl, indenyl, benzocyclobutenyl groups, . . . .

"Heterocycle" means a saturated, unsaturated or aromatic, condensed, spiro-condensed or bridged, monocyclic or bicyclic system with 3 to 12 members, comprising from 1-4 heteroatoms, either identical or different, selected from oxygen, sulfur and nitrogen, and possibly containing 1 or 2 oxo (=O) or thioxo (=S) groups, it being understood that in the case of a bicyclic system, one of the cycles may be aromatic and the other cycle is aromatic or unsaturated. A heterocycle for example comprises the piperidyl, piperazyl, furyl, thienyl, pyrrolyl, pyrazolyl, imidazolyl, pyridyl, pyrimidyl, pyrazinyl, pyradizinyl, benzofuryl, benzothienyl, indolyl, quinolyl, isoquinolyl, benzodioxolyl, benzodioxinyl, benzo[1,2,5]thiadiazolyl, benzo[1,2,5]oxadiazolyl, [1,2,3]triazolyl, [1,2,4]triazolyl groups, . . . .

"Alkylthio" means a —SAlk group wherein Alk is an alkyl group as defined earlier. Alkylthio for example comprises methylthio, ethylthio, isopropyltio, heptylthio, . . . .

"Arylalkyl" means an -Alk-Ar group wherein Alk represents an alkyl group as defined earlier, and Ar represents an aryl group as defined earlier.

"Halogen atom" means a fluorine, bromine, chlorine or iodine atom.

"Cycloalkyl" means a saturated monocyclic or polycyclic system, such as a condensed or bridged bicyclic system, comprising 3 to 12 carbon atoms such as the cyclopropyl, cyclobutyl, cyclopentyl, cyclohexyl, cycloheptyl, cyclooctyl, adamantyl, decalinyl, norbornyl groups, . . . .

"Cycloalkenyl" means an unsaturated monocyclic or polycyclic system such as a condensed or bridged bicyclic system, comprising from 3 to 12 carbon atoms such as the cyclopropenyl, cyclobutenyl, cyclopentenyl, cyclohexenyl groups, . . . .

"Monoalkylamino" means a —NHAlk group wherein Alk is an alkyl group as defined earlier.

"Dialkylamino" means a —NAlkAlk' group wherein Alk and Alk' each represent independently of each other an alkyl group as defined earlier.

"Monoalkylamide" means a —C(O)NHAlk group wherein Alk is an alkyl group as defined earlier.

"Dialkylamide" means a —C(O)NAlkAlk' group wherein Alk and Alk' each represent independently of each other an alkyl group as defined earlier.

"N-cycloalkyl" means a cycloalkyl radical as defined earlier, comprising a nitrogen atom, connected to the remainder of the molecule through this atom. N-cycloalkyl for example comprises the piperid-1-yl or pyrrolid-1-yl group.

"N-cycloalkenyl" means a cycloalkenyl radical as defined earlier, comprising a nitrogen atom, connected to the remainder of the molecule through this atom. N-cycloalkenyl for example comprises the tetrahydropyridin-1-yl group.

"Ester" means a —C(O)O$R_c$ group with $R_c$ representing an alkyl group as defined earlier.

"Haloalkyl" means a linear or branched saturated hydrocarbon chain, comprising from 1 to 6 carbon atoms and substituted with one or more, and notably 1 to 6 halogen atoms, such as the trifluoromethyl, 2,2,2-trifluoroethyl groups, . . . .

"Haloalkoxy" means a linear or branched saturated hydrocarbon chain comprising from 1-6 carbon atoms and substituted with one or more, and notably 1 to 6 halogen atoms, said chain being connected to the compound through an oxygen atom, such as the trifluoromethoxy, 2,2,2-trifluoroethoxy groups, . . . .

"Haloalkylthio" means a linear or branched saturated hydrocarbon chain, comprising from 1-6 carbon atoms and substituted with one or more, and notably 1-6 halogen atoms, said chain being attached through a sulfur atom such as the trifluoromethylthio group, . . . .

"Protective group" or "protection group" means the group which selectively blocks the reactive site in a multifunctional compound so that a chemical reaction may be carried out selectively at another non-protected reactive site, with the meaning conventionally associated with the latter in synthesis chemistry.

"Isomerism" means compounds which have identical molecular formulae but which differ by nature or in the binding sequence of their atoms or in the layout of their atoms in space. Isomers which differ in the layout of their atoms in space are designated by "stereoisomers". Stereoisomers which are not mirror images of each other, are designated as "diastereoisomers", and stereoisomers which are non-superposable mirror images of each other are designated as "enantiomers" or optical isomers. "Stereoisomers" refer to racemates, enantiomers, and diastereoisomers.

"Pharmaceutically acceptable" means which is generally safe and non-toxic, and which is not biologically undesirable, both for veterinary use and for human pharmaceutical use.

"Pharmaceutically acceptable salts" of a compound means salts which are pharmaceutically acceptable, as defined herein, and which have the desired pharmacological activity of the parent compound. It should be understood that all the references to pharmaceutically acceptable salts comprise the addition forms of solvents (solvates) or crystalline forms (polymorphous forms) as defined herein, of the same acid or base addition salt. A review of pharmaceutically acceptable salts is notably described in *J. Pharm. Sci.*, 1977, 66, 1-19.

The "pharmaceutically acceptable acids" mean the salts of non-toxic acids derived from organic or mineral acids. Among pharmaceutically acceptable acids, mention may be made in a non-limiting way, of hydrochloric, hydrobromic, sulfuric, phosphonic, nitric, acetic, trifluoroacetic, lactic, pyruvic, malonic, succinic, glutaric, fumaric, tartaric, maleic, citric, ascorbic, oxalic, methane-sulfonic, camphoric, benzoic, toluene-sulfonic acids, . . . .

The "pharmaceutically acceptable bases" mean non-toxic basic salts derived from organic or mineral bases, formed when an acid proton present in the parent compound is replaced by a metal ion or is coordinated to an organic base. Among pharmaceutically acceptable bases, mention may be made in a non-limiting way, to sodium hydroxide, potassium hydroxide, lithium hydroxide, calcium hydroxide, triethylamine, tertbutylamine, 2-diethylaminoethanol, ethanolamine, ethylenediamine, dibenzylethylenediamine, piperidine, pyrrolidine, morpholine, piperazine, benzylamine, arginine, lysine, histidine, glucosamine, quaternary ammonium hydroxides, . . . .

In the present patent application, the chemical compounds are named according to the IUPAC (The International Union of Pure and Applied Chemistry) nomenclature when the latter may be applied to said compound.

The object of the present invention is compounds of formula (I):

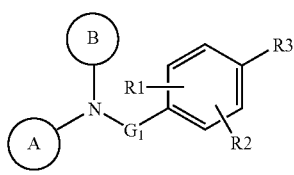

(I)

as well as their stereoisomers,
wherein:
$G_1$ represents a group

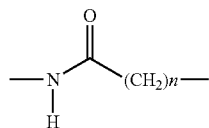

wherein n is an integer comprised between 1 and 4, preferably n has the value 1, R1 and R2 either identical or different, each represent independently of each other a group selected from a hydrogen atom, a halogen atom, a hydroxyl (—OH), thio (—SH), alkoxy, haloalkoxy, alkylthio, haloalkylthio, amino ($NH_2$), monoalkylamino, dialkylamino, cycloakyl, alkyl or haloalkyl group, R3 represents:
a group

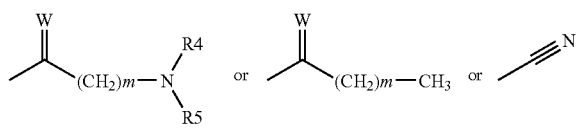

wherein:
W represents an oxygen, sulfur atom or NH,
m is an integer comprised between 0 and 5, and
R4 and R5 represent independently of each other a hydrogen atom, a linear or branched alkyl group or an alkoxy group,
or one of the following groups:

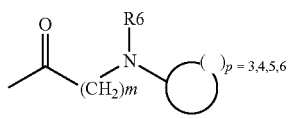

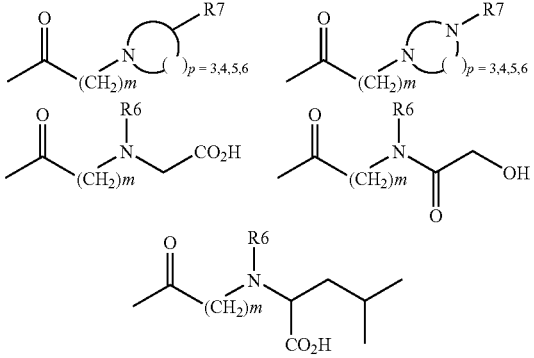

wherein:
R6 represents a hydrogen atom or a linear or branched alkyl group,
R7 represents a hydrogen atom, a linear of branched alkyl group, an acyl group, —$COCH_2OH$, —$CH_2COOH$ or —$(CH_2)_2NH_2$,
m is an integer comprised between 0 and 5,
the groups indicated below have the following meaning:

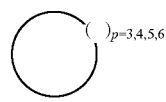

represents a monocyclic cycloalkyl with 3, 4, 5 or 6 apices;

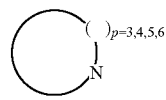

represents a monocyclic heterocycle with 3, 4, 5 or 6 apices including a nitrogen atom;

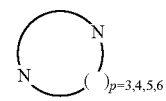

represents a monocyclic heterocycle with 3, 4, 5 or 6 apices including two nitrogen atoms;

A represents an aryl group, such as a phenyl, optionally substituted:
  in the meta or para position with:
    a halogen atom or an alkyl, haloalkyl, cyano (—CN), acyl, alkoxy, haloalkoxy, acylaminoalkyl group or a group —XR wherein X represents —O—, —NH—, —N(Alk)-, —N($COCH_3$)—, —S—, —SO—, —$SO_2$—, —CO— or —CONH— and R represents an arylalkyl, cycloalkyl or aryl group, each optionally substituted with one or two substituents, either identical or different, such as a halogen atom, an alkoxy, alkyl, haloalkyl, cyano, acyl, amino, monoalkylamino or dialkylamino group, or a cycloalkyl, aryl, arylalkyl, or heterocycle group, preferably N-cycloalkyl, each being optionally substituted with one or two substituents, either identical or different, such as a halogen atom, an alkoxy, alkyl, haloalkyl, cyano, acyl, amino, monoalkylamino, or dialkylamino group, an acid group (—CO₂H), an ester, amide (—CONH₂), mono- or di-alkylamide group, or a group —SOnR', —OCOR', —NR'COR'', or —NR'SO₂R'', wherein R' and R'' each represent independently of each other a hydrogen atom, an alkyl or haloalkyl group, and n has the value 1 or 2, and/or in the ortho or meta position with an alkyl group, and B represents an aryl group, preferably a phenyl:
substituted in the ortho position with a N-cycloalkyl group, such as piperidine, or with a cyclohexyl, each optionally substituted with one or more substituents, either identical or different, selected from an alkyl, haloalkyl, alkoxy, haloalkoxy, oxo, —X'-aryl group wherein X' represents —O—, —NH—, —N(Alk)-, —N(COCH₃)—, —S—, —SO—, —SO₂—, —CO— or —CONH—, and/or optionally substituted with a halogen atom or with an alkyl or haloalkyl group.

The present invention also relates to pharmaceutically acceptable salts of the compounds of formula (I).

According to a first aspect, R1 advantageously represents a alkoxy group, such as methoxy, preferably in the ortho position, relatively to R3.

According to a second aspect, R2 advantageously represents a hydrogen or halogen atom, such as chlorine or bromine, or an alkyl group such as methyl, preferably in the meta position relatively to R3. Preferably R2 will represent a halogen atom, such as bromine, preferably in the meta position relatively to R3.

According to a third aspect, A represents an aryl group, such as phenyl, optionally substituted:
in the meta or para position with:
a halogen atom of a cyano, acyl, alkoxy, haloalkoxy, acylaminoalkyl or —XR group wherein X represents —O—, —S—, —SO—, —SO₂— or —CO— and R represents an arylalkyl, cycloalkyl or aryl group, each optionally substituted with one or two substituents, either identical or different, such as a halogen atom, an alkoxy or acyl group, or
a cycloalkyl, aryl or arylalkyl group, each optionally substituted with one or two substituents, either identical or different, such as an acyl or alkoxy group,
and/or in the ortho or meta position with an alkyl group.

Preferably, A represents an aryl group, such as a phenyl, substituted, preferably in the para position, with an alkoxy group, such as methoxy, or an acyl group, such as acetyl.

According to a fourth aspect, B represents an aryl group, preferably a phenyl,
substituted in the ortho position with a heterocycle, preferably a N-cycloalkyl, such as a piperidine group, and optionally substituted in the ortho' position with an alkyl group, such as methyl.

The preferred compounds are the compounds of formula (I) wherein:
R1 represents an alkoxy group, such as methoxy, preferably in the ortho position relatively to R3,
R2 represents a hydrogen or halogen atom, such as chlorine or bromine, or an alkyl group, such as methyl, preferably in the meta position relatively to R3, and
R3, A and B are as defined earlier.

Another group of preferred compounds of formula (I) is the one wherein:
R3 represents:
a group:

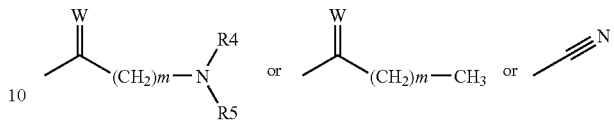

and advantageously

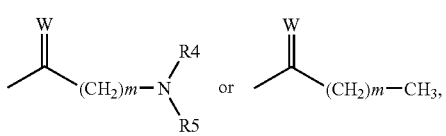

wherein:
W represents an oxygen atom or NH,
m is an integer comprised between 0 and 2, and
R4 and R5 represent independently of each other a hydrogen atom, a linear or branched alkyl group, such as a methyl or tertiobutyl, or an alkoxy group, such as a methoxy,
or the group:

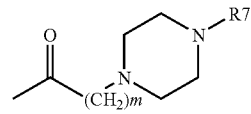

wherein R7 is as defined earlier and preferably represents an alkyl group, such as methyl, and m represents an integer comprised between 0 and 2,
and R1, R2, A and B are as defined earlier.

Another group of preferred compounds of formula (I) is the one wherein:
A represents an aryl group, such as a phenyl, optionally substituted:
in the meta or para position with:
a halogen atom or a cyano, acyl, alkoxy, haloalkoxy, acylaminoalkyl, or —XR group, wherein X represents —O—, —S—, —SO—, —SO₂— or —CO— and R represents an arylalkyl, cycloalkyl or aryl group, each optionally substituted with one or two substituents, either identical or different, such as a halogen atom, an alkoxy or acyl group, or
a cycloalkyl, aryl or arylalkyl group, each optionally substituted with one or two substituents, either identical or different, such as an acyl or alkoxy group, and
and/or in the ortho or meta position with an alkyl group, and B represents an aryl group, preferably a phenyl,
substituted in the ortho position with a heterocycle, preferably a N-cycloalkyl, such as a piperidine group, and/or substituted in the ortho' position with an alkyl group, such as a methyl,
and R1, R2 and R3 are as defined earlier.

Another group of preferred compounds of formula (I) is the one wherein:

R1 represents an alkoxy group, such as methoxy, preferably in the ortho position relatively to R3, R2 represents a halogen atom such as bromine, preferably in the meta position relatively to R3, R3 represents:

a group:

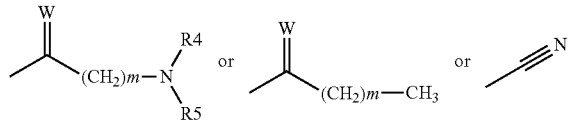

and advantageously

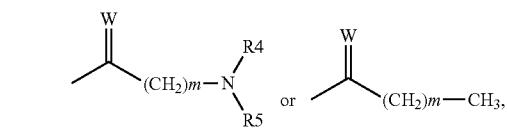

wherein:

W represents an oxygen atom or NH, m is an integer comprised between 0 and 2, and R4 and R5 represent independently of each other a hydrogen atom, a linear or branched alkyl group, such as a methyl or tertiobutyl, or an alkoxy group, or the group:

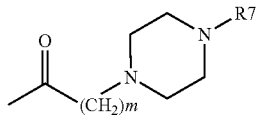

wherein R7 is as defined earlier, and preferably represents an alkyl group, such as methyl, and m is an integer comprised between 0 and 2, A represents an aryl group, such as phenyl, preferably substituted in the para position with an alkoxy group, such as methoxy, or an acyl group, such as acetyl, and B represents an aryl group, preferably a phenyl, substituted in the ortho position, with a heterocycle, preferably a N-cycloalkyl, such as a piperidine group, and/or substituted in the ortho' position with an alkyl group, such as a methyl.

A group of particularly preferred compounds of formula (I) is the one wherein:

R1 represents a methoxy group in the ortho position relatively to R3,

R2 represents a bromine atom in the meta position relatively to R3,

R3 represents:

a group:

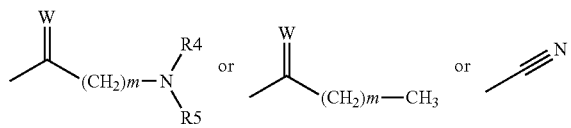

and advantageously

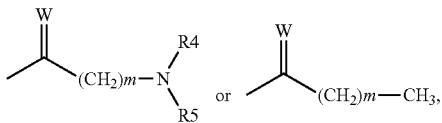

wherein:

W represents an oxygen atom or NH, m is an integer comprised between 0 and 2, and R4 and R5 represent independently of each other a hydrogen atom, a linear or branched alkyl group, such as a methyl or tertiobutyl, or an alkoxy group, or the group:

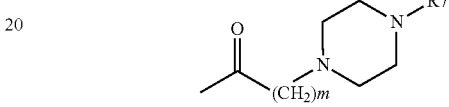

wherein R7 is as defined earlier, and preferably represents an alkyl group, such as methyl, and m is an integer comprised between 0 and 2, A represents a phenyl group substituted in the para position with a methoxy or acetyl group, and B represents a phenyl group substituted in the ortho position with a piperidine group and substituted in the ortho' position with a methyl group.

The still more preferred compounds are grouped in Table I:

TABLE I

| | |
|---|---|
| 1 | 5-Bromo-2-methoxy-4-[N'-(4-methoxy-phenyl)-N'-(2-methyl-6-piperidin-1-yl-phenyl)-hydrazinocarbonylmethyl]-benzamide |
| 2 | 5-Bromo-2-methoxy-4-[N'-(4-methoxy-phenyl)-N'-(2-methyl-6-piperidin-1-yl-phenyl)-hydrazinocarbonylmethyl]-N,N-dimethyl-benzamide |
| 3 | [2-Bromo-5-methoxy-4-(4-methyl-piperazine-1-carbonyl)-phenyl]-acetic acid N'-(4-methoxy-phenyl)-N'-(2-methyl-6-piperidin-1-yl-phenyl)-hydrazide |
| 4 | 4-[N'-(4-Acetyl-phenyl)-N'-(2-methyl-6-piperidin-1-yl-phenyl)-hydrazinocarbonylmethyl]-5-bromo-2-methoxy-benzamide |
| 5 | (4-Acetyl-2-bromo-5-methoxy-phenyl)-acetic acid N'-(4-methoxy-phenyl)-N'-(2-methyl-6-piperidin-1-yl-phenyl)-hydrazide |
| 6 | 5-Bromo-2-N-dimethoxy-4-[N'-(4-methoxy-phenyl)-N'-(2-methyl-6-piperidin-1-yl-phenyl)-hydrazinocarbonylmethyl]-N-methyl-benzamide |
| 7 | 5-Bromo-N-tert-butyl-2-methoxy-4-[N'-(4-methoxy-phenyl)-N'-(2-methyl-6-piperidin-1-yl-phenyl)-hydrazinocarbonylmethyl]-benzamide |
| 8 | (2-Bromo-4-cyano-5-methoxy-phenyl)-acetic acid N'-(4-methoxy-phenyl)-N'-(2-methyl-6-piperidin-1-yl-phenyl)-hydrazide |

An object of the present invention is also pharmaceutical compositions comprising at least one compound of formula (I) or a pharmaceutically acceptable salt thereof, in association with a pharmaceutically acceptable excipient.

The pharmaceutical compositions according to the invention may be compositions which may be administered into the body via any administration route. In a non-exhaustive way, the route for administering pharmaceutical compositions according to the invention may be topical, enteral or parenteral, preferably buccal, conjunctival, cutaneous, endotracheal, intradermal, intraepidermal, intramuscular, intravascular, laryngeal, nasal, ophthalmic, oral, rectal, respiratory, sub-cutaneous, transcutaneous or vaginal administration. It is generally advantageous to formulate such pharmaceutical compositions as unit doses. Each dose then comprises a predetermined amount of the active ingredient, associated with the suitable carrier, excipients and/or adjuvants, calculated in order to obtain a given therapeutic effect. As an example of a unit dose form which may be administered orally, mention may be made of tablets, gelatin capsules, granules, powders and oral solutions or suspensions. As an example of a unit dose form which may be administered topically (notably for local treatment of external genital and perianal verrucas), mention may be made of ovules, gels, creams, lotions, solutions and patches.

The suitable formulations for the selected administration form are known and described for example in Remington, The Science and Practice of Pharmacy, 19$^{th}$ edition, 1995, Mack Publishing Company, and may therefore be easily prepared by one skilled in the art.

It is known that dosage varies from one individual to the other, depending on the nature and the intensity of the affection, the selected administration route, the weight, the age and the gender of the patient, accordingly the effective doses should be determined depending on these parameters by the specialist in this matter. As an indication, the effective doses may range from 1 to 500 mg per day.

An object of the present invention is also a compound of formula (I) or a pharmaceutically acceptable salt thereof as defined earlier for its use as a drug.

An object of the present invention is also the use of the compounds of formula (I) or a pharmaceutically acceptable salt thereof for treating or preventing infection by the papilloma virus preferably in humans.

An object of the present invention is also the use of the compounds of formula (I) or of their pharmaceutically acceptable salts for inhibiting the replication of the papilloma virus by inhibition of the formation of the protein complex E1/E2.

An object of the present invention is further the use of the compounds of formula (I) or of their pharmaceutically acceptable salts for preparing a drug intended for treating or preventing an infection by the papilloma virus preferably in humans.

An object of the present invention in particular is the use of compounds of formula (I) or of their pharmaceutically acceptable salts for preparing a drug intended for treating or preventing an infection by a low risk papilloma virus such as HPV6, HPV7, HPV11, HPV13, HPV32, HPV34, HPV40, HPV42, HPV43, HPV44, HPV53, HPV54, HPV55, HPV57, HPV58, HPV74, HPV91.

An object of the present invention is in particular the use of the compounds of formula (I) or their pharmaceutically acceptable salts for preparing a drug intended for treating or preventing an infection by HPV6 and/or HPV11.

Thus, an object of the present invention is also the use of the compounds of formula (I) or of their pharmaceutically acceptable salts for preparing a drug intended for treating or preventing lesions and diseases associated with infections by the papilloma virus.

An object of the present invention is in particular the use of compounds of formula (I) or of their pharmaceutically acceptable salts for preparing a drug intended for treating or preventing ano-genital verrucas such as acuminated condylomas and planar condylomas, laryngeal, conjunctival or buccal papillomas and other epithelial lesions such as recurrent respiratory papillomatoses and low grade and high grade intra-epithelial neoplasias, bowenoid papuloses, (vulgar, plantar, myrmecias, superficial, flat . . . ) verrucas, verruciform epidermaldysplasias, carcinomas, in particular ano-genital carcinomas, and all the lesions which are associated with the papilloma virus.

An object of the present invention in particular is the use of the compounds of formula (I) or of their pharmaceutically acceptable salts for preparing a drug intended for treating or preventing ano-genital verrucas, such as acuminated condylomas and planar condylomas, laryngeal, conjunctival or buccal papillomas and other epithelial lesions, such as recurrent respiratory papillomatoses and low grade intra-epithelial neoplasias and all the lesions which are associated with the papilloma virus.

The compounds, objects of the present invention, may be prepared according to the synthesis route described hereafter, by using precursors of the following formulae (II) and (III),

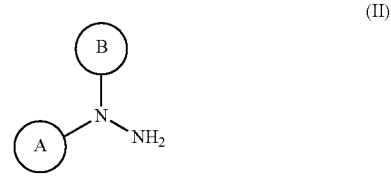

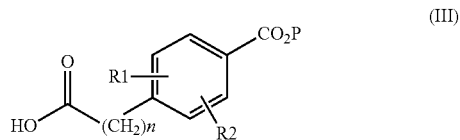

wherein n, A, B, R1 and R2 are as defined earlier, and P represents a protecting group of an acid function, such as a linear or branched ($C_1$-$C_4$)alkyl group.

According to this synthesis route, peptide coupling is carried out between the compounds (II) and (III) for example in the presence of EDCI in a basic and polar medium in order to lead to the compound of formula (IV):

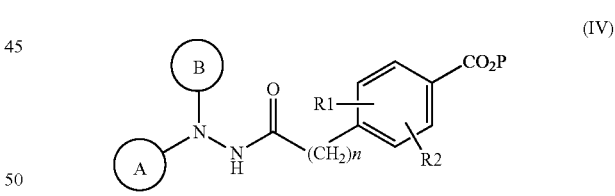

Next, the group —$CO_2P$ of the compound of formula (IV) is de-protected by hydrolysis, in order to obtain the following compound of formula (V):

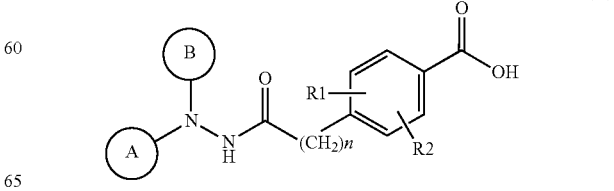

In the case when in the group corresponding to R3, m=0, the compounds of formula (I) may be obtained by reacting the terminal diversely substituted amine of R3 either directly on the acid function of the compound of formula (V), or on one of its activated forms, for example obtained by reaction of the compound of formula (V) with N-hydroxysuccinimide or with oxalyl chloride.

In the case when in the group corresponding to R3, m≠0, the compounds of formula (I) may be obtained by passing through the enol ether intermediate from the corresponding ester of formula (IV) for example by using Tebbe's reagent. This enol ether intermediate is then submitted to a Mannich reaction, with for example paraformaldehyde in the presence of dimethylamine in a polar solvent, which leads to the product of formula (I) in the case when m≠0.

The compounds of formula (I) may also be obtained from precursors of the following formulae (II) and (X):

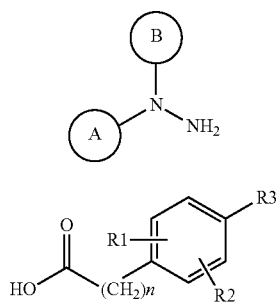

(II)

(X)

wherein, n, A, B, R1, R2 and R3 are as defined earlier.

In this case, peptide coupling is carried out between the compounds (II) and (X) for example in the presence of EDCI in a basic and polar medium in order to lead to the compound of formula (I) as described earlier.

The precursor of formula (II) may be obtained from the compound of the following formula (VI):

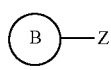

(VI)

wherein B is as defined earlier and Z is a halogen such as fluorine or bromine.

In the case when Z is a fluorine, the compound of formula (VI) is submitted to an aromatic nucleophilic substitution in a basic and polar medium in the presence of the compound of the following formula (VII):

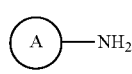

(VII)

wherein A is as defined earlier, in order to obtain the compound of the following formula (VIII):

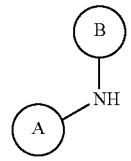

(VIII)

wherein A and B are as defined earlier.

In the case when Z is a bromine, the compound of formula (VI) is submitted to a Buchwald reaction in the presence of bis(2-diphenylphosphinophenyl)ether and of a catalyst such as tris(dibenzylideneacetone)dipalladium(0) in a basic and apolar medium in the presence of the compound (VII) as defined earlier in order to lead to the compound of formula (VIII) as defined earlier.

The compound of formula (VIII) is put into the presence of sodium nitrite in an acidic medium and then reduced by a hydride, for example lithium aluminium hydride, in order to obtain the compound of formula (II) as defined earlier.

In the case when R2 represents a hydrogen atom, the compound of formula (III) may be obtained according to methods of the literature (*J. Med. Chem.*, 1998, 41, 5219 or WO 0135900).

In the case when R2 represents a bromine atom, the compound of formula (III) may be obtained by reacting dibromine in an acidic medium with a precursor of the following formula (IX):

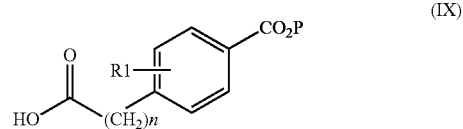

(IX)

wherein R1, n and P are as defined earlier.

The compounds of formula (VI) and (VII) are either commercial compounds, or compounds obtained according to known methods of organic synthesis, easily accessible and understandable by one skilled in the art.

In the preferred case when B is a phenyl substituted with a piperidine, the compounds of formula (I) may be prepared according to the following synthesis route.

The compound of formula (II) may be obtained from the compound of formula (XI):

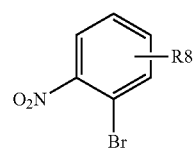

(XI)

wherein R8 may be a halogen atom, an alkyl or haloalkyl group.

The compound of formula (XI) is submitted to a Buchwald reaction in the presence of bis(2-diphenylphosphinophenyl) ether and of a catalyst, as defined above, in a basic and apolar medium in the presence of the compound (VII) as defined earlier:

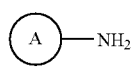

(VII)

and the compound of the following formula (XII) is obtained:

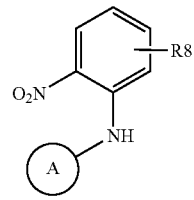

(XII)

wherein A and R8 are as defined earlier.

The compound of formula (XII) is reduced by tin chloride in a polar medium (*Tet. Lett.* 1984, 25(8), 839) and then reacted with a dibromoalkane, for example dibromopentane in a basic and apolar medium (*Bioorg. Med. Chem. Lett.* 1996, 6(5), 563) in order to lead to the compound of formula (XIII):

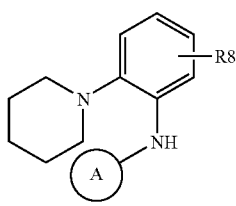

(XIII)

wherein A and R8 are as defined earlier.

The compound of formula (XIII) is put into the presence of sodium nitrite in an acidic medium and then reduced by a hydride, for example lithium aluminium hydride, in order to obtain the compound of formula (II) as defined earlier:

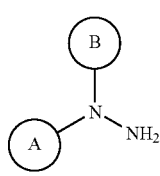

(II)

The following examples illustrate the invention but do not by any means limit it.

The starting products used are commercial products or products prepared according to known operating procedures from commercial products or known to one skilled in the art. The different preparations lead to synthesis intermediates useful for preparing the compounds of the invention.

The structures of the compounds described in the examples and in the preparations were determined according to usual spectrophotometric techniques (nuclear magnetic resonance (NMR), mass spectrometry (MS) including electrospray (ES), . . . ) and purity was determined by high performance liquid chromatography (HPLC).

The abbreviations used in the operating procedures:
TLC: thin layer chromatography
EDCI: 1-(3-dimethylaminopropyl)-3-ethylcarbodiimide hydrochloride
DMSO: dimethylsulfoxide
DMF: dimethylformamide
NaCl: sodium chloride
DIPEA: N,N-diisopropylethylamine
HOBt: 1-hydroxybenzotriazole
TFA: trifluoroacetic acid
THF: tetrahydrofurane
DPEPhos: bis(2-diphenylphosphinophenyl)ether
NaOH: sodium hydroxide
HCl: hydrochloric acid
$Na_2CO_3$: sodium carbonate
TEBBE reagent: an olefination reagent of formula $Cp_2Ti=CH_2$
Cp: cyclopentadienyl

PREPARATION 1 methyl 4-carboxymethyl-2-methoxy-benzoate

Methyl 4-carboxymethyl-2-methoxy-benzoate may be prepared according to the method described in *J. Med. Chem.* 1998, 41, 5219 or patent WO 0135900.

PREPARATION 2 methyl 5-bromo-4-carboxymethyl-2-methoxy-benzoate

Methyl 5-bromo-4-carboxymethyl-2-methoxy-benzoate is obtained from preparation 1 according to the procedure described in patent WO 0135900.

EXAMPLE 1

5-bromo-2-methoxy-4-[(N'-(4-methoxy-phenyl)-N'-(2-methyl-6-piperidin-1-yl-phenyl)-hydrazinocarbonylmethyl]-benzamide (1)

Stage 1: (4-methoxy-phenyl)-(2-methyl-6-nitro-phenyl)amine

To a solution of 50 g of 2-fluoro-3-nitrotoluene in 1.1 L of DMSO are added at room temperature 59.5 g of para-anisidine (1.5 equivalents). After 5 minutes of stirring at room temperature, 57.9 g of potassium tert-butanoate (1.6 equivalents) are added to the reaction medium and the whole is heated to 110° C. for 1 hour. The reaction medium is directly hydrolyzed by adding 1 L of ice and water and then the aqueous phase is extracted several times with ethyl acetate. The organic phases are collected, dried on sodium sulphate, filtered and then dry concentrated. The raw product is chromatographed on silica gel (ether/cyclohexane:0/100, 5/95 and then 20/80) in order to provide 34.95 g of the expected compound as a dark red solid.

Yield: 42%

$^1$H NMR (CDCl$_3$, 400 MHz) δ(ppm): 8.52 (broad s, 1H), 7.98 (d. 1H), 7.36 (d, 1H), 6.97 (1H), 6.80 (s, 4H), 3.79 (d, 3H), 2.00 (s, 3H)

Stage 2: $N^2$-(4-Methoxy-phenyl)-3-methyl-benzene-1,2-diamine

To a solution of 72.0 g of the compound obtained earlier in 900 mL of ethanol are added under argon 314.5 g of tin chloride (5 equivalents). The reaction medium is refluxed for 2 hours. The medium is then cooled to room temperature and then concentrated under reduced pressure. The whole is taken up in 600 mL of ethyl acetate and 300 mL of water. The medium is then basified up to a pH of 8 with a 50% NaOH solution. Both phases are separated and the aqueous phase is extracted several times with ethyl acetate. The organic phases are collected, dried on sodium sulphate, filtered and dry evaporated. 52.27 g of the expected compound are obtained as a brown solid. The product is engaged without additional purification in the following step.

Yield: 90%

$^1$H NMR (CDCl$_3$, 400 MHz) δ(ppm): 7.01 (t, 1H), 6.77 (d, 2H), 6.67 (m, 2H), 6.56 (d, 2H), 3.76 (s, 3H), 2.18 (s, 3H)

Stage 3: (4-Methoxy-phenyl)-(2-methyl-6-piperidin-1-yl-phenyl)-amine

To a solution of 50.0 g of the compound obtained earlier, in 800 mL of anhydrous toluene are successively added 92.0 mL of DIPEA (2.4 equivalents), 29.85 mL of 1,5-dibromopentane (1.0 equivalent) and 5 g of sodium iodide (about 10% by mass). The medium is refluxed with stirring, under argon, for 12 hours. The reaction raw product is diluted in 500 mL of water and the resulting aqueous phase is extracted several times with ethyl acetate. The organic phases are collected, dried on sodium sulphate, filtered and dry concentrated. The raw product is chromatographed on silica gel (ethyl acetate/cyclohexane:2/98) in order to provide 22.75 g of expected compound as a brown solid.

Yield: 36%

$^1$H NMR (CDCl$_3$, 400 MHz) δ(ppm): 6.97 (m, 3H), 6.77 (d, 2H), 6.70 (d, 2H). 6.16 (broad s, 1H), 3.77 (s, 3H), 2.74 (m, 4H), 2.09 (s, 3H), 1.61 (m, 4H), 1.53 (m, 2H)

Stage 4: N-Nitroso-(4-methoxy-phenyl)-N-(2-methyl-6-piperidin-1-yl-phenyl)-amine To a 10° C. thermostated solution of 20.6 g of the previous compound in 250 mL of acetic acid is added dropwise a solution of 27.81 g of sodium nitride (5.8 equivalents) in 250 mL of water. The medium is left under stirring at room temperature, under argon, for 25 minutes. The raw product is diluted in 200 mL of water and then the resulting aqueous solution is poured over about 100 g of solid sodium carbonate. The aqueous phase is extracted several times with dichloromethane and the organic phases are collected, dried on sodium sulphate and then dry evaporated. 20.0 g of raw product are obtained and then engaged into the next step without any additional purification.

Yield: 87%

$^1$H NMR (CDCl$_3$, 400 MHz) δ(ppm): 7.29 (m, 3H), 6.99 (d, 2H), 6.90 (d, 2H), 3.84 (s, 3H), 2.67 (m, 2H), 2.52 (m, 2H), 1.95 (s, 3H), 1.36 (m, 4H), 1.25 (m, 2H)

Stage 5: N-(4-Methoxy-phenyl)-N-(2-methyl-6-piperidin-1-yl-phenyl)-hydrazine To a solution of 7.0 g of the previous compound in 85 mL of anhydrous ether is slowly added under argon a 1 N solution of 86.05 mL of lithium aluminium hydride in ether (4 equivalents). The reaction medium is refluxed with stirring for 1 hour at the end of which the reaction is completed (monitored with TLC). The reaction raw product is neutralized by adding dropwise 100 mL of ethyl acetate and 200 mL of water. The aqueous phase is extracted several times with ethyl acetate and the organic phases are collected, dried on sodium sulphate, filtered and dry concentrated. The raw product is chromatographed on silica gel (ethyl acetate/cyclohexane:1/99) in order to provide 4.61 g of expected compound as a orange-red powder.

Yield: 69%

$^1$H NMR (CDCl$_3$, 400 MHz) δ(ppm): 7.14 (t, 1H). 6.99 (dd, 2H), 6.77 (s, 4H), 4.90 (broad s, 2H), 3.76 (s, 3H), 2.80 (m, 4H), 2.09 (s, 3H), 1.57 (m, 6H)

Stage 6: Methyl 5-bromo-2-methoxy-4-[N'-(4-methoxy-phenyl)-N''-(2-methyl-6-piperidin-1-yl-phenyl)-hydrazinocarbonylmethyl]-benzoate To a solution of 5.28 g of compound obtained previously in 60 mL of DMF are successively added, 5.65 g of compound obtained in preparation 2 (1.1 equivalents), 2.52 g of HOBt (1.1 equivalents), 3.57 g of EDCI (1.1 equivalents) and 2.35 mL of triethylamine (1.0 equivalent). After 15 minutes of stirring at 100° C., the reaction is completed (monitored with TLC). The reaction medium is cooled and then poured on ice. The formed precipitate is filtered and then taken up in dichloromethane. The resulting organic phase is dried on sodium sulphate, filtered and dry evaporated. The raw product is chromatographed on silica gel (ethyl acetate/cyclohexane:1/9) in order to provide 8.81 g of expected compound as a brown powder.

Yield: 87%

$^1$H NMR (CDCl$_3$, 400 MHz) δ(ppm): 10.06 and 9.92 (2s, 1H). 8.02 and 7.98 (2s, 1H), 7.19 (m, 1H), 7.02 (m, 2H), 6.91 (s, 1H), 6.75 (m, 2H), 6.54 (d, 2H), 3.89 (s, 3H), 3.87 and 3.78 (m, 2H), 3.74 (s, 6H), 3.71 (m, 2H), 2.79 (m, 2H), 2.40 (s. 3H), 1.45 (m, 6H)

Stage 7: 5-Bromo-2-methoxy-4-[N'-(4-methoxy-phenyl)-N'-(2-methyl-6-piperidin-1-yl-phenyl)-hydrazinocarbonylmethyl]-benzoic acid hydrochloride To a solution of 6.99 g of the compound obtained previously in 160 mL of THF is added a solution of 850 mg of lithium hydroxide (3 equivalents) in 50 mL of water. The medium is left under stirring at room temperature and under argon for 12 hours. THF is then evaporated under reduced pressure and a 1 M hydrochloric acid solution is added dropwise. The formed precipitate is filtered, washed with a 1 M hydrochloric acid solution and then taken up in dichloromethane. After evaporation of the solvent under reduced pressure, the pale yellow solid is purified by chromatography on silica gel (dichloromethane/methanol: 98/2 to 95/5). The resulting white powder is then solubilized in a minimum of THF/water (1:4) mixture and then re-precipitated by dropwise addition of a 1 M hydrochloric acid solution. The formed precipitate is filtered, washed with a 1 M hydrochloric acid solution and dried in vacuo at 35° C. for 48 hours. 4.35 g of the expected compound are obtained as a white solid.

Yield: 60%

HPLC: 98.6%

MS: MH$^+$ 582/584

$^1$H NMR (DMSO+TFA, 400 MHz) δ(ppm): 7.90 (d, 1H), 7.79 (s, 1H), 7.68 (t, 1H), 7.61 (d, 1H), 7.26 (s, 1H), 6.88 (d, 2H), 6.62 (d, 2H), 4.14 (d, 1H), 3.95 (m, 2H). 3.76 (s, 3H), 3.69 (s, 3H), 3.42 (m, 1H), 3.30 (d, 1H), 3.16 (d, 1H), 2.21 (s, 3H), 1.85 (m, 4H), 1.48 (m, 2H)

Stage 8: 2,5-Dioxo-pyrrolidin-1-yl 5-bromo-2-methoxy-4-[N'-(4-methoxy-phenyl)-N'-(2-methyl-6-piperidin-1-yl-phenyl)-hydrazinocarbonylmethyl]-benzoate To a solution of 117 mg of the compound obtained previously in 570 μL of dichloromethane, are consecutively added at room temperature, 80 μL of triethylamine (3.0 equivalents), 32 mg of N-hydroxysuccinimide (1.5 equivalents) and then 54 mg of EDCI (1.5 equivalents). After 18 hours of stirring, the reaction medium is diluted in 10 mL of chloroform. The resulting organic phase is washed several times with water and then with a saturated NaCl solution, dried on sodium sulphate, dry evaporated. The raw product is chromatographed on silica gel (dichloromethane/methanol:98/2) in order to provide 76 mg of the expected compound as a white solid which is engaged into the next step without any additional purification.
Yield: 59%

Stage 9: 5-Bromo-2-methoxy-4-[N'-(4-methoxy-phenyl)-N'-(2-methyl-6-piperidin-1-yl-phenyl)-hydrazinocarbonylmethyl]-benzamide (1)

50 mg of a solution of the compound obtained previously in 500 μl of dioxane is purged under argon. A stream of ammonia gas is maintained for 30 minutes at room temperature and then the reaction medium is stirred for 2 hours and then dry evaporated. The obtained white solid is taken up into 10 ml of ethyl acetate. The resulting organic phase is washed several times with water, with a saturated NaCl solution, dried on sodium sulphate, dry evaporated. The raw product is chromatographed on silica gel (dichloromethane/methanol:98/2) in order to provide 36 mg of the expected compound as a white solid.
Yield: 83
HPLC: 96.3%
MS: MH$^+$ 581/583
$^1$H NMR (DMSO+TFA, 200 MHz) δ(ppm): 7.95 (s, 1H), 7.91 (s, 1H), 7.67 (m, 3H), 7.26 (s, 1H), 6.91 (d, 2H), 6.61 (d, 2H), 3.75-4.16 (m+dd, 3H), 3.84 (s, 3H), 3.70 (s, 3H), 3.10-3.45 (m, 3H), 2.20 (s. 3H), 1.45-1.92 (m, 6H)

EXAMPLE 2

5-Bromo-2-methoxy-4-[N'-(4-methoxy-phenyl)-N'-(2-methyl-6-piperidin-1-yl phenyl)-hydrazinocarbonylmethyl]-N,N-dimethyl-benzamide (2)

To a solution of 85 mg of the compound obtained in stage 8 of Example 1 in 500 μL of THF are added at room temperature 2 mL (29 equivalents) of a 2 M dimethylamine solution in THF. The reaction medium is then stirred for 2 hours before being dry evaporated. The obtained white solid is taken up in 10 mL of ethyl acetate. The resulting organic phase is washed several times with water and then with a saturated NaCl solution, dried on sodium sulphate, dry evaporated. The raw product is chromatographed on silica gel (dichloromethane/methanol:98/2) in order to provide 45 mg of the expected compound as a white solid.
Yield: 53%
HPLC: 97%
MS: MH$^+$ 609/611
$^1$H NMR (DMSO+TFA, 200 MHz) δ(ppm): 7.91 (d, 1H), 7.70 (m, 2H), 7.38 (s, 1H), 7.19 (s, 1H), 6.88 (d, 2H), 6.81 (d, 2H), 4.09 (d, 1H), 3.93 (m, 1H), 3.88 (d, 1H), 3.75 (s, 3H), 3.70 (s, 3H), 3.10-3.50 (m, 3H), 2.95 (s, 3H), 2.75 (s, 3H), 2.20 (s, 3H), 1.65-1.95 (m, 4H), 1.49 (m, 2H)

EXAMPLE 3

[2-Bromo-5-methoxy-4-(4-methyl-piperazine-1-carbonyl)phenyl]-acetic acid N'-(4-methoxy-phenyl)-N'-(2-methyl-6-piperidin-1-yl-phenyl)-hydrazide (3)

To 92 mg of a solution of the compound obtained in stage 8 of Example 1 in 450 μL of dichloromethane, are added at room temperature 82 μL of N-methylpiperazine (5 equivalents). The reaction medium is stirred for 2 hours before being dry evaporated. The obtained white solid is taken up in 10 mL of ethyl acetate. The resulting organic phase is washed several times in water and then with a saturated NaCl solution, dried on sodium sulphate, dry evaporated. The raw product is chromatographed on silica gel (dichloromethane/methanol:98/2) in order to provide 53 mg of the expected compound as a white solid.
Yield: 54%
HPLC: 98.1%
MS: MH$^+$ 664/666
$^1$H NMR (DMSO+TFA, 200 MHz) δ(ppm): 9.55 (s, 1H), 7.38 (s, 1H), 6.99-7.20 (m, 4H), 6.79 (d, 2H), 6.50 (d, 2H), 3.54-3.80 (m, 2s, m, 11H), 3.10 (m, 2H), 2.70 (m, 1H), 2.30 (m, 4H), 2.22 (s, 3H), 2.16 (s, 3H), 1.40 (m, 4H), 1.25 (m, 2H)

EXAMPLE 4

4-[N'-(4-Acetyl-phenyl)-N'-(2-methyl-6-piperidin-1-yl-phenyl)-hydrazino-carbonylmethyl]-5-bromo-2-methoxy-benzamide (4)

Stage 1: 1-[4-(2-Methyl-6-nitro-phenylamino)-phenyl]-ethanone

In a flask under an argon atmosphere are consecutively placed 2.16 g of 2-bromo-3-nitrotoluene, 1.69 g of 4-aminoacetophenone (1.25 equivalents), 229 mg of dipalladium trisdibenzylideneacetone (0.025 equivalents), 269 mg of DPEPhos (0.05 equivalents) and 4.07 g of cesium carbonate (1.25 equivalents). The toluene is added at room temperature. The heterogeneous reaction medium is purged with argon and refluxed for hours. After returning to room temperature, water and ethyl acetate are added. After separation of the phases, the organic phase is washed with water and then with a saturated NaCl solution, dried on sodium sulphate, filtered and then dry evaporated. The obtained red oil is purified by chromatography on silica (ethyl acetate/cyclohexane:5/95 to 10/90) in order to provide 2.29 g of the expected compound as a red oil.
Yield: 85%
$^1$H NMR (CDCl$_3$, 200 MHz) δ(ppm): 7.95 (m, 4H), 7.51 (d, 1H), 7.19 (d, 1H), 6.68 (d, 2H), 2.53 (s, 3H), 2.17 (s, 3H)

Stage 2: 1-[4-(2-Amino-6-methyl-phenylamino)-phenyl]-ethanone

The product (2.02 g) is obtained according to the method of stage 2 of Example 1, by using 2.29 g of the previous derivative as starting product and 9.56 g of tin chloride in 30 mL of ethanol.
Yield: 99%
$^1$H NMR (CDCl$_3$, 200 MHz) δ(ppm): 7.81 (d, 2H), 7.06 (t, 1H), 6.68 (d, 2H), 6.55 (d, 2H), 5.42 (broad s, 1H), 2.50 (s, 3H), 2.15 (s, 3H)

Stage 3: 1-(4-(2-Methyl-6-piperidin-1-yl-phenylamino)-phenyl]-ethanone

The product (1.36 g) is obtained according to the method of stage 3 of Example 1, by using 2.02 g of the previous derivative as a starting product, 3.5 mL of DIPEA, 1.20 mL of 1,5-dibromopentane and 200 mg of sodium iodide.
Yield: 52
$^1$H NMR (CDCl$_3$, 200 MHz) δ(ppm): 7.84 (d, 2H), 7.08 (d, 1H), 6.97 (m, 2H), 6.64 (d, 2H), 6.35 (broad s, 1H), 2.72 (m, 4H), 2.52 (s, 3H), 2.14 (s, 3H), 1.55 (m, 6H)

Stage 4: [4-(2-Methyl-[1,3]dithian-2-yl)-phenyl]-(2-methyl-6-piperidin-1-yl-phenyl)amine To a solution of 1.36 g of the compound obtained previously in 22 mL of dichloromethane are successively added at room temperature 550 μL of 1,3-propanedithiol (1.25 equivalents) and then 920 μL of boron trifluoride etherate (1.5 equivalents). After 18 hours of stirring at room temperature, the reaction is stopped by adding 50 mL of a 2 M NaOH solution. After separation of the phases, the aqueous phase is extracted several times with dichloromethane. The organic phases are collected, washed with a saturated NaCl solution, dried on sodium sulphate, filtered and then dry evaporated in order to provide 1.55 g of the expected compound as a white foam.

Yield: 89%
$^1$H NMR (CDCl$_3$, 200 MHz) δ(ppm): 7.67 (d, 2H), 6.99 (m, 3H), 6.67 (d, 2H), 2.77 (m, 8H), 2.14 (s, 3H), 1.95 (m, 2H), 1.87 (s, 3H), 1.66 (m, 4H), 1.53 (m, 2H)

Stage 5: N-nitroso-[4-(2-methyl-[1,3]dithian-2-yl)-phenyl]-(2-methyl-6-piperidin-1-yl-phenyl)amine To a solution of 856 mg of the compound obtained previously in 6 mL of acetic acid are added dropwise a solution of 1.17 g of sodium nitrite (5.8 equivalents) in 6 mL of water. A precipitate is formed which is dissolved by successively adding 6 mL of dichloromethane and 6 mL of methanol. The reaction medium is left under stirring at room temperature, under argon, for 2 hours and then poured on 10 g of solid sodium carbonate. The raw product is diluted with 40 mL of water and 40 mL of dichloromethane. The phases are separated and then the aqueous phase is extracted several times with dichloromethane. The organic phases are collected, dried on sodium sulphate, and then dry evaporated in order to provide 839 mg of the expected product as a pale red foam. This nitroso derivative is engaged in the following step without any additional purification.

Yield: 91%
$^1$H NMR (CDCl$_3$, 200 MHz) δ(ppm): 7.93 (d, 2H), 7.33 (m, 3H), 7.00 (t, 2H), 2.49-2.77 (m, 8H), 1.99 (m, 2H), 1.96 (s, 3H), 1.81 (s, 3H), 1.33 (m, 4H), 1.19 (m, 2H)

Stage 6: N-[4-(2-Methyl-[1,3]dithian-2-yl)-phenyl]-N-(2-methyl-6-piperidin-1-yl-phenyl)-hydrazine The product (333 mg) is obtained according to the method of stage 5 of Example 1, by using 836 mg of the previous derivative as a starting product and 8 mL of a 1 M lithium aluminium hydride solution in diethylether.

Yield: 41%
$^1$H NMR (CDCl$_3$, 200 MHz) δ(ppm): 7.64 (d, 2H), 7.18 (m, 1H), 6.99 (t, 2H), 6.79 (d, 2H), 2.78 (m, 8H), 2.10 (s, 3H), 1.93 (m, 2H), 1.86 (s, 3H), 1.56 (m, 6H)

Stage 7: Methyl 5-bromo-2-methoxy-4-[(N'-[4-(2-methyl-[1,3]dithian-2-yl)-phenyl]-N'-(2-methyl-6-piperidin-1-yl-phenyl)-hydrazinocarbonylmethyl]-benzoate The product (320 mg) is obtained according to the method of stage 6 of Example 1, by using 333 mg of the previous hydrazine and 267 mg of the acid of preparation 2 in the presence of 119 mg of HOBt, 169 mg of EDCI and 130 μL of triethylamine in 2.4 mL of DMF.

Yield: 57%
$^1$H NMR (CDCl$_3$, 200 MHz) δ(ppm): 9.76 (s, 1H), 8.00 (s, 1H), 7.67 (d, 2H), 6.92-7.21 (m, 4H), 6.57 (d, 2H), 3.91 (m, 2H), 3.96 (s, 3H), 3.73 (s, 3H), 2.71 (m, 6H), 2.43 (s, 3H), 2.36 (m, 2H), 1.93 (m, 2H), 1.78 (s, 3H), 1.22-1.44 (m, 6H)

Stage 8: Methyl 4-[N'-(4-acetyl-phenyl)-N'-(2-methyl-6-piperidin-1-yl-phenyl)-hydrazinocarbonylmethyl]-5-bromo-2-methoxy-benzoate To a solution of 320 mg of the compound obtained previously in 5 mL of a THF/water mixture (9:1) are consecutively added at room temperature, 204 mg of mercury(II) oxide (2.0 equivalents) and then 130 μL of boron trifluoride etherate (2.0 equivalents). Stirring is continued for 16 hours and then the reaction is stopped by adding 20 mL of a 2 M soda solution. The resulting aqueous phase is extracted several times with ethyl acetate. The organic phases are collected, washed with water and with a saturated NaCl solution, dried on sodium sulphate, filtered and then dry evaporated. The raw product is chromatographed on silica gel (chloroform 100%) in order to provide 210 mg of the expected compound as a white solid.

Yield: 73%
$^1$H NMR (CDCl$_3$, 200 MHz) δ(ppm): 9.78 (s, 1H), 7.98 (s, 1H), 7.82 (d, 2H), 7.21 (d, 1H), 7.01 (t, 2H), 6.88 (s, 1H), 6.60 (d, 2H), 3.85 (s, 3H), 3.75 (m, 2H), 3.73 (s, 3H), 2.72 (m, 2H), 2.36-2.49 (s+m+s, 8H), 1.39 (m, 6H)

Stage 9: [N'-(4-acetyl-phenyl)-N'-(2-methyl-6-piperidin-1-yl-phenyl)-hydrazinocarbonylmethyl]-5-bromo-2-methoxy-benzoic acid To a solution of 210 mg of the compound obtained previously in 3.5 mL of THF are added at room temperature, 41 mg of lithium hydroxide (5 equivalents) in solution in 1.4 mL of water. A white solid precipitates in the reaction medium which is solubilized by adding 500 μL of methanol. Stirring is continued for 18 hours and then the reaction medium is diluted in 50 mL of ethyl acetate. The resulting organic phase is washed with water and then with a saturated NaCl solution, dried on sodium sulphate, dry evaporated. The raw product is chromatographed on silica gel (dichloromethane/methanol: 96/4) in order to provide 142 mg of the expected compound as a white foam.

Yield: 69%
HPLC: 96.3%
MS: MH$^+$ 594/596
$^1$H NMR (CDCl$_3$, 200 MHz) δ(ppm): 9.98 (s, 1H), 8.36 (s, 1H), 7.82 (d, 2H), 7.25 (s, 1H), 7.03 (m, 3H), 6.60 (d, 2H), 3.94 (s, 3H), 3.78 (s, 2H), 2.80 (m, 2H), 2.37-2.51 (s+m+s, 8H), 1.57 (m, 6H)

Stage 10: 4-[N'-(4-acetyl-phenyl)-N'-(2-methyl-6-piperidin-1-yl-phenyl)-hydrazinocarbonylmethyl)-5-bromo-2-methoxy-benzamide (4)

To a solution of 75 mg of the previous compound in 200 μL of THF are successively added at room temperature, 20 mg of HOBt, 28 mg of EDCI (1.1 equivalents) and then 300 μL (4.8 equivalents) of 2 M ammonia solution in THF. The reaction medium is stirred at room temperature for 18 hours and then diluted with ethyl acetate. The resulting organic phase is washed several times with water and then with a saturated NaCl solution, dried on sodium sulphate, filtered and dry evaporated. The raw product is chromatographed on silica gel (dichloromethane/methanol:98/2) in order to provide 70 mg of the expected compound as a whitish solid. A fraction of the obtained white foam is solubilized in 1 mL of diethylether. After adding 100 µL of a 4 M hydrochloric acid solution in dioxane, and then filtration, the hydrochloride of the expected compound is obtained as a white solid.

Yield (neutral form): 93%
HPLC: 96.75%
MS: MH+ 593/595
$^1$H NMR—hydrochloride form—(DMSO, 200 MHz) δ(ppm): 7.92 (m, 4H), 7.69 (m, 4H), 7.36 (s, 1H), 6.74 (broad s, 2H), 4.04-4.28 (dd+m, 3H), 3.86 (s, 3H), 3.16-3.56 (m, 3H), 2.24 (s, 3H), 1.77 (m, 4H), 1.46 (m, 2H).

EXAMPLE 5

(4-Acetyl-2-bromo-5-methoxy-phenyl)-acetic acid N'-(4-methoxy-phenyl)-N'-(2-methyl-6-piperidin-1-yl-phenyl)-hydrazide (5)

Stage 1: [2-Bromo-5-methoxy-4-(1-methoxy-vinyl)-phenyl]-acetic acid N'-(4-methoxy-phenyl)-N'-(2-methyl-6-piperidin-1-yl-phenyl)-hydrazide To a solution of 200 mg of the compound obtained in stage 6 of Example 1 in 2 mL of THF are added at room temperature, 177 µL of a 4 M solution of TEBBE's reagent in toluene. After 20 hours of stirring at room temperature, the reaction medium is basified with 15 mL of a saturated Na$_2$CO$_3$ solution and then the aqueous phase is extracted with ethyl acetate (3×20 mL). The organic phases are collected, dried on sodium sulphate, filtered and dry concentrated. The raw product is chromatographed on silica gel (cyclohexane/ethyl acetate: 90/10) in order to provide 138 mg of expected compound as a white solid.

Yield: 68%
MS: MH+ 593/595

Stage 2: (4-Acetyl-2-bromo-5-methoxy-phenyl)-acetic acid N'-(4-methoxy-phenyl)-N'-(2-methyl-6-piperidin-1-yl-phenyl)-hydrazide (5)

To a solution of 138 mg of the compound obtained previously in 2 mL of THF is added 1 mL of 1N HCl solution. After 4 hours of stirring at room temperature, the reaction medium is basified with 20 mL of a saturated Na$_2$CO$_3$ solution and then the aqueous phase is extracted with ethyl acetate (3×20 mL). The organic phases are collected, dried on sodium sulphate, filtered and then dry concentrated. The raw product is chromatographed on silica gel (cyclohexane/ethyl acetate: 80/20) in order to provide 96mg of the expected compound as a beige solid.

Yield: 74%
HPLC: 96.26%
MS: MH+ 579/581
$^1$H NMR (CD$_3$OD, 200 MHz) δ(ppm): 7.80 (s, 1H), 7.00-7.3 (m, 4H), 6.65 (dd, 4H), 3.83 (s+m, 8H), 3.72 (s, 3H), 2.75 (m, 2H), 2.56 (s, 3H), 2.35 (s+m, 5H), 1.15-1.45 (m, 6H)

EXAMPLE 6

5-Bromo-2-N-dimethoxy-4-[N'-(4-methoxy-phenyl)-N'-(2-methyl-6-piperidin-1-yl-phenyl)hydrazinocarbonylmethyl]-N-methyl-benzamide (6)

To a suspension of 200 mg of the compound obtained in stage 7 of Example 1 in neutral form in 3 mL of anhydrous dichloromethane are added dropwise at 0° C., 30 µL of methane sulfonyl chloride. The medium then becomes homogenous. After 20 minutes of stirring at 0° C., 38 mg of N,O-dimethylhydroxylamine hydrochloride are added to the reaction medium and the whole is placed under stirring at 0° C. for 30 minutes more at the end of which the reaction is not completed (according to monitoring with TLC). An additional amount of 38 mg of N,O-dimethylhydroxylamine hydrochloride is then added and the reaction medium is placed under stirring at room temperature for 1 hour. The medium becomes heterogeneous and appears as a white suspension. The raw reaction product is then hydrolyzed with 10 mL of water and then the resulting aqueous phase is extracted with dichloromethane (3×20 mL). The organic phases are collected, dried on sodium sulphate, filtered and dry concentrated. The raw product is chromatographed on silica gel (cyclohexane/ethyl acetate: 90/10) in order to provide 60 mg of the expected compound as a beige solid.

Yield: 29%
MS: MH+ 624/626
$^1$H NMR (DMSO+TFA, 200 MHz) δ(ppm): 7.60-7.95 (m, 3H), 7.47 (s, 1H), 7.20 (s, 1H), 6.75 (dd, 4H), 3.80-4.15 (m, 3H), 3.74 (s, 3H), 3.71 (s, 3H), 3.10-3.55 (m, 9H), 2.20 (s, 3H), 1.40-1.95 (m, 6H).

EXAMPLE 7

5-Bromo-N-tert-butyl-2-methoxy-4-[N'-(4-15 methoxy-phenyl)-N'-(2-methyl-6piperidin-1-yl-phenyl)hydrazinocarbonylmethyl]-benzamide (7)

To a suspension of 300 mg of the compound obtained in stage 7 of Example 1 in neutral form in 4 mL of anhydrous dichloromethane are successively added 120 µL of oxalyl chloride, 3 drops of DMF. The medium having become homogenous is stirred, at room temperature, under argon, for 1 hour before being dry evaporated and then again placed under argon. The raw reaction product is then diluted in 4 mL of dichloromethane before adding dropwise 72 µL of tert-butylamine. After 1 hour of stirring at room temperature, the reaction medium is basified with 20 mL of a saturated Na$_2$CO$_3$ solution and then the aqueous phase is extracted with ethyl acetate (3×30 mL). The organic phases are collected, dried on sodium sulphate, filtered and dry concentrated. The raw product is chromatographed on silica gel (cyclohexane/ethyl acetate: 80/20) in order to provide 95 mg of the expected compound as a beige solid.

Yield: 29%
MS: MH+ 636/638
$^1$H NMR (DMSO+TFA, 200 MHz) δ(ppm): 7.60-7.95 (m, 6H), 7.26 (s, 1H), 6.75 (dd, 4H), 3.95-4.10 (m, 6H), 3.85 (s, 3H), 3.70 (s, 3H), 3.10-3.50 (m, 3H), 2.21 (s, $^3$H), 1.40-1.95 (m, 6H), 1.35 (s, 9H).

EXAMPLE 8

(2-Bromo-4-cyano-5-methoxy-phenyl)-acetic acid N'-(4-methoxy-phenyl)-N'-(2-methyl-6-piperidin-1-yl-phenyl)hydrazide (8)

To a suspension of 490 mg of the compound obtained in stage 9 of Example 1 in 4 mL of anhydrous dichloromethane are successively added at −78° C., 96 µL of DMSO and 128 mg of oxalyl chloride. After 15 minutes of stirring at −78° C., 350 µL of triethylamine are slowly added to the reaction medium at −78° C. After 30 minutes of additional stirring at −78° C., the reaction medium is hydrolyzed with 10 mL of water and the aqueous phase is then extracted with dichloromethane (3×15 mL). The resulting organic phase is dried on sodium sulphate, filtered and dry concentrated. The raw product is chromatographed on silica gel (cyclohexane/ethyl acetate: 80/20) in order to provide 356 mg of the expected compound as a white powder.

Yield: 75%

MS: MH+ 562/564

$^1$H NMR (DMSO+TFA, 200 MHz) δ(ppm): 8.08 (s, 1H), 7.60-7.95 (m, 3H), 7.40 (s, 3H), 6.75 (dd, 4H), 3.95-4.20 (m, 3H), 3.88 (s, 3H), 3.70 (s, 3H), 3.10-3.50 (m, 3H), 2.20 (s, 3H), 1.40-1.90 (m, 6H).

Biological Activity Results

The activity of the molecules against the papilloma virus may be evaluated in different tests in vitro and cell tests like those described by Chiang et al. (1992), *Proc. Natl. Acad. Sci. USA*, 89:5799-5803 or further by White et al. (2003), *Journal of Biological Chemistry*, 278: 26765-26772.

EXAMPLE 9

Pharmacological Studies of the Compounds of the Invention in Cell Tests of Interaction Between Viral Proteins E1 and E2 and of Replication of Viral DNA of the HPVs A first series of tests evaluates the interaction between the proteins E1 and E2 of HPVs in human cells. A second series of tests measures the replication of viral genomic DNA in human cells.

The tests of interaction between E1 and E2 are related to the tests often called 'mammalian 2 Hybrid' tests. They are based on co-transfection of a reporter vector containing DNA binding sites for the protein E2 in the promoter containing the expression of the reporter gene, and of expression vectors coding for the proteins E1 and E2 of HPV, the proteins E1 being fusioned to the PV16 transactivation domain. With these tests, it is possible to monitor the interaction between the proteins E1 and E2, this interaction being a step required for replication of the genome of the HPVs.

The tests of replication of viral genomic DNA are based on the co-transfection of a reporter vector containing a viral replication origin (ori) and expression vectors coding for the proteins E1 and E2 of HPV. They allow monitoring of the whole of the biological functions of E1 and E2 required for replicating the genome of the HPVs.

For the interaction tests between E1 and E2, a reporter vector was built containing several DNA binding sites for the protein E2 (the palindrome 5' ACCGNNNNCGGT-3') upstream from the minimum promoter MLP (Adenovirus Major Late Promoter) controlling the transcription of the gene coding for firefly luciferase. Vectors were also built for expressing the proteins E1 of HPVs, fusioned at the N-termini with the PV16 transactivator domain of the HSV-1 virus. Co-transfection of this reporter vector containing E2 sites and of vectors expressing the proteins E1 of HPVs leads to a marginal increase in the luciferase activity. Co-transfection of this reporter vector containing E2 sites, of vectors expressing E2 proteins of HPVs and of vectors expressing E1 proteins fusioned in the PV16 domain enables formation in the cells of the strongly transactivating protein complex E2/E1-PV16, and leads to strong increase in luciferase activity. This expresses the interaction between the E1 and E2 proteins in the cells.

For tests of replication of viral genomic DNA, a reporter vector, 'replicon' was built containing the viral replication origin of HPV11/HPV6 (also called LCR which bear binding sites of the E1 and E2 proteins of the HPV) and the gene coding for the firefly luciferase under the transcriptional control of the promoter of SV40. It was checked that the presence of the replication origin of the HPV does not have any transcriptional effect on the expression of the gene of the luciferase, this either in the presence or in the absence of the viral proteins E1 or E2. Co-transfection of this replicon-vector and of vectors expressing the E1 and E2 proteins of HPV leads to an increase in luciferase activity depending on the presence of E1 and of E2 and expresses the increase in the number of reporter vectors. This is due to the activity of the viral proteins E1 and E2 which allow replication in mammal cells of this replicon-vector containing a viral replication origin.

The chemical compounds were evaluated for their inhibitory activity of the formation of the interaction between the E1 and E2 proteins of HPV11/HPV6 in cell tests by co-transfecting, in human cell lines derived from kidney epithelial or cervical carcinoma cells, the reporter vector containing binding sites for E2 and pairs of vectors for expressing the HPV11/HPV6 proteins, either E1 fusioned to PV16 on the one hand, and E2 on the other hand. Varied doses of the compounds were incubated for 1-4 days after the transfection in the cell medium and luciferase activity was determined by means of a luminometer in order to evaluate the IC$_{50}$ of the compounds on the formation of the interaction between the E1 and E2 proteins of the HPVs.

The chemical compounds 1 and 4 of Table 1 were also evaluated for their inhibitory activity of viral replication depending on E1 and E2 of HPV11/HPV6 in these cell tests by co-transfecting, in human cell lines derived from kidney epithelial or cervical carcinoma cells, the replicon-reporter vector and pairs of vectors for expressing E1 and E2 of HPV11/HPV6. Varied doses of the compounds were incubated for 2-6 days after transfection in the cell medium and luciferase activity was determined with a luminometer in order to evaluate the IC$_{50}$ of the compounds on the replication of the genome of the HPVs.

All the compounds presented in the examples above inhibit the formation of the interaction between the E1 and E2 proteins of HPV11/HPV6 in cells with an IC$_{50}$ of less than 20 μM, and for the preferred compounds, of less than 10 μM. Those evaluated in the viral replication tests inhibit dependent replication of E1 and E2 of HPV11/HPV6 in cells with an IC$_{50}$ of less than 20 μM, or even less than 10 μM for the most active compounds.

The invention claimed is:

1. A compound of formula (I):

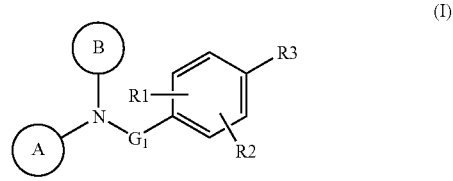

as well as its stereoisomers and its pharmaceutically acceptable salts, wherein:
G₁ represents a group

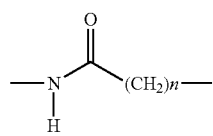

wherein n is an integer comprised between 1 and 4,
R1 and R2 either identical or different, each represent independently of each other a group selected from a hydrogen atom, a halogen atom, a hydroxyl, thio, alkoxy, haloalkoxy, alkylthio, haloalkylthio, amino, monoalkylamino, dialkylamino, cycloakyl, alkyl or haloalkyl group,
R3 represents:
a group

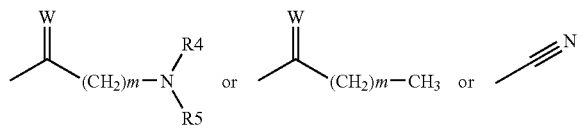

wherein:
W represents an oxygen, sulfur atom or NH,
m is an integer comprised between 0 and 5 and
R4 and R5 represent independently of each other a hydrogen atom, a linear or branched alkyl group or an alkoxy group,
or one of the following groups:

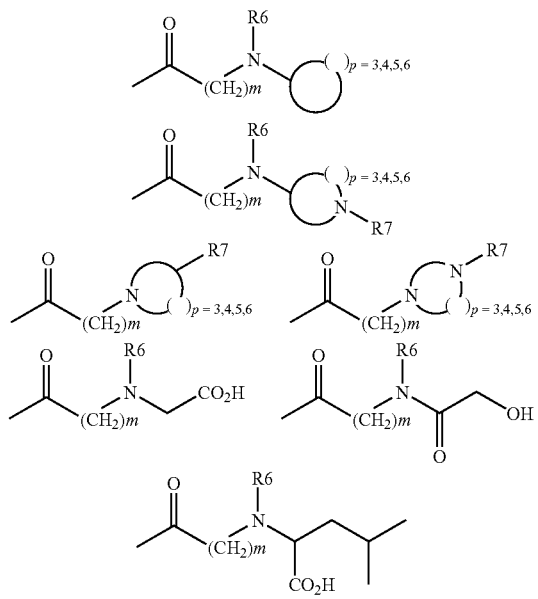

wherein:
R6 represents a hydrogen atom or a linear or branched alkyl group,
R7 represents a hydrogen atom, a linear of branched alkyl group, acyl, —COCH₂OH, —CH₂COOH or —(CH₂)₂NH₂,
m is an integer comprised between 0 and 5, the groups indicated above have the following meaning:

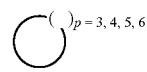

represents a monocyclic cycloalkyl with 3, 4, 5 or 6 apices;

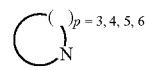

represents a monocyclic heterocycle with 3, 4, 5 or 6 apices including a nitrogen atom;

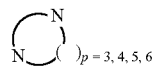

represents a monocyclic heterocycle with 3, 4, 5 or 6 apices including two nitrogen atoms;
A represents an aryl group, optionally substituted:
in the meta or para position with:
a halogen atom or an alkyl, haloalkyl, cyano, acyl, alkoxy, haloalkoxy, acylaminoalkyl group or a group —XR wherein X represents —O—, —NH—, —N(Alk)-, —N(COCH₃)—, —S—, —SO—, —SO₂—, —CO— or —CONH— and R represents an arylalkyl, cycloalkyl or aryl group, each optionally substituted with one or two substituents, either identical or different, or
a cycloalkyl, aryl, arylalkyl, or heterocycle group, each being optionally substituted with one or two substituents, either identical or different,
and/or in the ortho or meta position with an alkyl group, and
B represents an aryl group:
substituted in the ortho position with a N-cycloalkyl group, or with a cyclohexyl, each optionally substituted with one or more substituents, either identical or different, selected from an alkyl, haloalkyl, alkoxy, haloalkoxy, oxo, —X'-aryl group wherein X' represents —O—, —NH—, —N(Alk)-, —N(COCH₃)—, —S—, —SO—, —SO₂—, —CO— or —CONH—, and/or
optionally substituted with a halogen atom or with an alkyl or haloalkyl group.

2. The compound according to claim 1, wherein:
R1 represents an alkoxy group,
R2 represents a hydrogen or halogen atom, or an alkyl group, and
R3, A and B are as defined in claim 1.

3. The compound according to claim 1, wherein:
R3 represents:
a group:

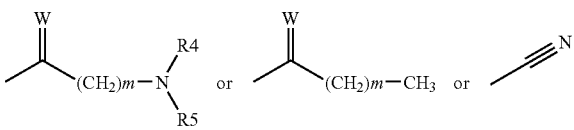

wherein:
W represents an oxygen atom or NH,
m is an integer comprised between 0 and 2, and
R4 and R5 represent independently of each other a hydrogen atom, a linear or branched alkyl group, or an alkoxy group,
or the group:

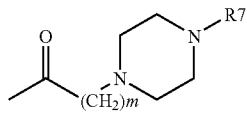

wherein R7 is as defined as in claim 1, and m is an integer between 0 and 2,
and R1, R2, A and B are as defined in claim 1.

4. The compound according to claim 1, wherein:
A represents an aryl group, optionally substituted:
  in the meta or para position with:
    a halogen atom or a cyano, acyl, alkoxy, haloalkoxy, acylaminoalkyl or —XR group wherein X represents —O—, —S—, —SO—, —SO$_2$— or —CO— and R represents an arylalkyl, cycloalkyl or aryl group, each optionally substituted with one or two substituents, either identical or different, a halogen atom, an alkoxy or acyl group or
    a cycloalkyl, aryl or arylalkyl group, each optionally substituted with one or two substituents, either identical or different, and/or
  in the ortho or meta position with an alkyl group, and
B represents an aryl group,
  substituted in the ortho position with a heterocycle, and/or
  substituted in the ortho' position with an alkyl group,
and R1, R2 and R3 are as defined in claim 1.

5. The compound according to claim 1, wherein:
R1 represents an alkoxy group,
R2 represents a halogen atom,
R3 represents:
a group:

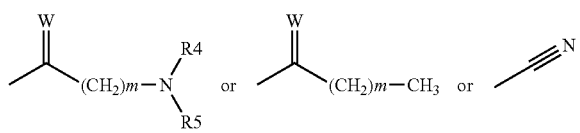

wherein:
W represents an oxygen atom or NH,
m is an integer comprised between 0 and 2, and
R4 and R5 represent independently of each other a hydrogen atom, a linear or branched alkyl group, or an alkoxy group,
or the group:

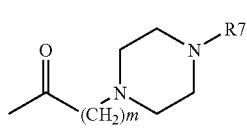

wherein R7 is as defined in claim 1 and m is an integer comprised between 0 and 2, A represents an aryl group, optionally substituted in the para position with an alkoxy or acyl group, and
B represents an aryl group,
  substituted in the ortho position with a heterocycle, and/or
  substituted in the ortho position with an alkyl group.

6. The compound according to claim 1, selected from the following group:
  1) 5-Bromo-2-methoxy-4-[N'-(4-methoxy-phenyl)-N'-(2-methyl-6-piperidin-1-yl-phenyl)-hydrazinocarbonylmethyl]-benzamide;
  2) 5-Bromo-2-methoxy-4-[N'-(4-methoxy-phenyl)-N'-(2-methyl-6-piperidin-1-yl-phenyl)-hydrazinocarbonylmethyl]-N,N-dimethyl-benzamide;
  3) [2-Bromo-5-methoxy-4-(4-methyl-piperazine-1-carbonyl)-phenyl]-acetic acid N'-(4-methoxy-phenyl)-N'-(2-methyl-6-piperidin-1-yl-phenyl)-hydrazide;
  4) 4-[N'-(4-Acetyl-phenyl)-N'-(2-methyl-6-piperidin-1-yl-phenyl)-hydrazino-carbonylmethyl]-5-bromo-2-methoxy-benzamide;
  5) (4-Acetyl-2-bromo-5-methoxy-phenyl)-acetic acid N'-(4-methoxy-phenyl)-N'-(2-methyl-6-piperidin-1-yl-phenyl)-hydrazide;
  6) 5-Bromo-2-N-dimethoxy-4-[N'-(4-methoxy-phenyl)-N'-(2-methyl-6-piperidin-1-yl-phenyl)-hydrazinocarbonylmethyl]-N-methyl-benzamide; and
  7) 5-Bromo-N-tert-butyl-2-methoxy-4-[N'-(4-methoxy-phenyl)-N'-(2-methyl-6-piperidin-1-yl-phenyl)-hydrazinocarbonyl-methyl]-benzamide.

7. A pharmaceutical composition comprising at least one compound of formula (I) according to claim 1 or a pharmaceutically acceptable salt thereof, in association with a pharmaceutically acceptable excipient.

8. A method of treating an infection by the papilloma virus or of inhibiting the replication of the papilloma virus comprising the administration to a person in need thereof of a compound of formula (I) according to claim 1 or of a pharmaceutically acceptable salt thereof.

9. A method for treating a pathology related to the papilloma virus comprising the administration to a person in need thereof of a compound of formula (I) according to claim 1 or of a pharmaceutically acceptable salt thereof.

10. The method according to claim 8, wherein said pathology is selected from ano-genital verrucas, laryngeal, conjunctival or buccal papillomas and other epithelial lesions.

11. The method according to claim 10, wherein the ano-genital verrucas are selected from acuminated condylomas and planar condylomas and the epithelial lesions are selected from recurrent respiratory papillomatoses and low grade and high grade intra-epithelial neoplasias, bowenoid papuloses, verrucas, verruciform epidermaldysplasias, carcinomas, and all the lesions which are associated with the papilloma virus.

12. The method according to claim 11, wherein the verrucas are selected from vulgar, plantar, myrmecias, superficial and flat verrucas and the carcinomas are ano-genital carcinomas.

13. The compound according to claim 1, wherein n has the value 1.

14. The compound according to claim 1, wherein A represents an aryl group, optionally substituted:
  in the meta or para position with:
    a halogen atom or an alkyl, haloalkyl, cyano, acyl, alkoxy, haloalkoxy, acylaminoalkyl group or a group —XR wherein X represents —O—, —NH—, —N(Alk)-, —N(COCH$_3$)—, —S—, —SO—, —SO$_2$—, —CO— or —CONH— and R represents an arylalkyl, cycloalkyl or aryl group, each optionally substituted with one or two substituents, either identical or different, selected from a halogen atom, an alkoxy, alkyl, haloalkyl, cyano, acyl, amino, monoalkylamino or dialkylamino group, or a cycloalkyl, aryl, arylalkyl, or heterocycle group, each being optionally substituted with one or two substituents, either identical or different, selected from a halogen atom, an alkoxy, alkyl, haloalkyl, cyano, acyl, amino, monoalkylamino, or dialkylamino, acid, ester, amide, mono- or di-alkylamide group, or a group —SOnR', —OCOR', —NR'COR", or —NR' SO$_2$R", wherein R' and R" each represent independently of each other a hydrogen atom, an alkyl or haloalkyl group, and n has the value 1 or 2, and/or in the ortho or meta position with an alkyl group.

15. The compound according to claim 2, wherein R1 is in the ortho position relative to R3.

16. The compound according to claim 2, wherein R2 is in the meta position relative to R3.

17. The compound according to claim 4, wherein A represents an aryl group, optionally substituted:
in the meta or para position with:
    a halogen atom or a cyano, acyl, alkoxy, haloalkoxy, acylaminoalkyl or —XR group wherein X represents —O—, —S—, —SO—, —SO$_2$— or —CO— and R represents an arylalkyl, cycloalkyl or aryl group, each optionally substituted with one or two substituents, either identical or different, selected from a halogen atom, an alkoxy or acyl group, or
    a cycloalkyl, aryl or arylalkyl group, each optionally substituted with one or two substituents, either identical or different, selected from an acyl or alkoxy group, and/or
in the ortho or meta position with an alkyl group.

* * * * *